United States Patent [19]

McRae

[11] Patent Number: Plant 6,557

[45] Date of Patent: Jan. 24, 1989

[54] LILY PLANT NAMED 'CRIMSON PIXIE'

[75] Inventor: Edward A. McRae, Boring, Oreg.

[73] Assignee: Melridge, Inc., Aurora, Oreg.

[21] Appl. No.: 51,823

[22] Filed: May 18, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new variety of hybrid lily plant having large clusters of flowers of excellent form and particularly characterized by their vivid red to red-orange coloration, broad tepals, and lack of spots. The plant is of short stature with moderately long and full leaves, and its upright flower orientation makes it especially suitable as a pot plant variety. The color pattern and silhouette of this new plant are completely new in the upright Asiatic divisions of lilies suited to forcing and to mass commercial cultivation. This new plant is highly resistant to disease and shows high tolerance of virus, it is an excellent garden plant with blooms having long persistence, and its bulbs may be precooled and forced through the year for pot plant production.

1 Drawing Sheet

BACKGROUND OF THE INVENTION

My new lily variety originated as a seedling selected from a group of seedlings planted by me at Sandy, Ore., with the object of producing new lilies having blooms in the shades of orange and red, well suited to forcing for pot plant production out-of-season. I achieved the desired objective by using as the seed parent the clonal cultivar 'Charisma' (U.S. Plant Pat. No. 4,180) and as the pollen parent, a short, complex hybrid of *L. dauricum* origin. This particular seedling was selected for propagation and test because of the large size, broad tepals, lack of spotting, and red to red-orange coloration of its blooms, a color pattern unique in this type of lily. This selected seedling was asexually reproduced by me and under my direction at Sandy, Ore., with such success that propagation was continued for several successive generations by bulb scale propagation as well as by natural propagation from bulblets, which demonstrated clearly that the novel and distinctive characteristics of this new variety will hold true from generation to generation and appear to be firmly fixed. The flowers of this new lily variety, characterized by large size, broad tepals, red to red-orange coloration, and lack of spotting, provide a color pattern that is unique in this type of lily. This plant remains short in stature and is not overly susceptible to bud abortion when forced into flower out-of-season as a pot plant. In addition, the clone possesses to a high degree great hardiness and disease resistance, as well as all of the desired characteristics of excellence of form, color, and habit.

The clone is vigorous and is a good grower and propagator as observed at Sandy, Ore. It is well suited to forcing out-of-season when the bulbs are dug at the appropriate time and properly precooled. October-dug bulbs properly precooled and potted in January will flower under glass in western Oregon in an average of about sixty to seventy-five days, with no supplementary lighting and at moderate greenhouse temperatures.

DESCRIPTION OF THE DRAWING

My new variety of lily plant is illustrated by the accompanying photographic drawing which shows a three-quarter view of the open bloom in full color and illustrates the flower form, the tepal arrangement, and the novel and distinctive red to red-orange unspotted flowers.

DESCRIPTION OF THE NEW VARIETY

The following is a detailed description of my new variety of Asiatic hybrid lily with nomenclature according to The International Lily Register of The Royal Horticulatural Society, Second Edition, 1969, and with color designations according to The R.H.S. Colour Chart published by The Royal Horticultural Society in 1966.

THE PLANT

Origin: Seedling.

Parentage:

- *Seed parent.*—Lilium 'Charisma' (U.S. Plant Pat. No. 4,180).
- *Pollen parent.*—A short, red, clonal selection from a complex, second generation *L. dauricum* cross.

Classification:

- *Botanic.*—Division I-A, Upright Asiatic Hybrid Lily, according to The Horticultural Classification of Lilies (The Royal Horticultural Society of London).
- *Commercial.*—Hybrid Lilium Clone.

Form: A single stem, erect and stately.

Height: Stems of about 35 to 55 cm. are produced by glasshouse forcing of bulbs of about 12 to 18 cm. in circumference, provided that their light levels are adequate. Low light levels may cause "stretching".

Growth: Upright and vigorous.

Foliage:

- *Quantity.*—Abundant.
- *Leaf size.*—About 8 to 12 cm. long and about 1 cm. wide.
- *Leaf shape.*—Lanceolate with acute tip.
- *Texture.*—Leathery.
- *Aspect.*—Glossy.
- *Color.*—Dark green on the upper side and somewhat lighter green on the lower side.

Bulbs:

- *Size.*—Various, ranging up to about 25 cm. in circumference for commercial use.
- *Color.*—White.

THE BUD

Form: Elliptic with rounded base and obtuse tip.

Size: About 8 to 9 cm. long and about 7 cm. in circumference just prior to opening.

Opening rate: The bud opens slowly, taking about an hour in response to morning light.

Color: Orange-Red, 34B-C, slightly lighter at the apex and base, just prior to opening and as the tepals begin to unfurl.

Peduncle:

*Length.*—Averages about 4 to 8 cm., but it may elongate if light levels are too low or if the bulbs have been improperly stored prior to forcing.

*Color.*—Dark green.

THE FLOWER

Blooming habit: Annually, once and profusely in mid-season.

Size: Medium, averaging about 12 to 17 cm. in diameter.

Borne: In a single compact raceme having 9 to 12 buds produced from a bulb of about 12 to 16 cm. in circumference.

Shape: Cup-shaped upon first opening and becoming flattened as the tepals recurve by the second day.

Tepalage:

*Number.*—Six, imbricated and hexagonally arranged.

*Size.*—Outer petals average about 2.5 to 3 cm. wide. Inner petals average about 3.5 to 4 cm. wide.

*Color.*—These flowers are distinguished by their vivid red to red-orange coloring, the base color being 43B to 43A-B. This color is produced by a magenta pigment in the upper epidermal cell layers of the tepals overlaying the red-orange pigmentation of the mesophyll layers. This causes the red color to vary somewhat under different light levels and to appear to be "brushed" more heavily in some areas of the tepals. The red-orange mesophyll color is Orange-Red, 33A-B, which also appears in a band about 1 to 2 mm. wide along the tepal margins. The nectaries are overlaid with white pubescence.

*Spotting.*—The tepals are unspotted.

*Appearance.*—Shiny.

*Longevity.*—The tepals stay on the stems for about three weeks.

*Color changes.*—The flower may become less red and more orange as it ages, depending upon light levels; there is usually only a slight change, if the light levels are adequate for cut flower and pot plant maintenance.

Pedicel:

*Length.*—About 5 to 12 cm., in average.

*Form.*—Sturdy and ascending up to about 60 degrees from the horizontal.

*Color.*—Dark green.

Disease resistance: The flower and plant are resistant to disease; in particular, they are resistant to Fusarium bulb rod and Botrytis blight as observed in western Oregon.

Fragrance: None.

Lasting quality: The flower is long lasting.

REPRODUCTIVE ORGANS

Stamens:

*Number.*—Six.

*Arrangement.*—Hexagonal and slightly overlapping.

*Anthers and pollen (dehisced).*—Color: Greyed Orange, 173A.

*Filaments.*—Length: About 5 cm. Color: Soft Red, 42B.

Pistils:

*Number.*—One.

*Length.*—About 5 cm.

*Stigma.*—Size: Medium (about 3 to 4 mm. in diameter). Color: Soft Plum, 46A.

Characteristics of ovary: The ovary is characteristic of the genus Lilium.

THE FRUIT

Fertility: The fruit is fertile.

Shape: Ovoid.

Color at maturity: Soft brown, sometimes overlaid with soft plum.

This new lily variety most closely resembles 'Red Carpet' (unpatented) but has a slightly lighter red to red-orange color which does not turn to brown as does 'Red Carpet'. The flower of the new plant has much broader and thicker tepals, a lighter pollen color, and the plant has a more compact inflorescence with shorter pedicels and a higher bud count. The new variety is also more reliable and uniform in its forcing performance and it can be forced into flower much more rapidly than 'Red Carpet'.

I claim:

1. The new and distinctive variety of Asiatic hybrid lily plant and parts thereof substantially as herein shown and described, characterized by its completely unspotted, broad tepalled, red to red-orange colored flowers, by its short stems, its longer and abundantly leaved foliage, and its upright flowering silhouette; and by the excellence of its flower form and versatility both as a garden plant and as a pot plant variety.

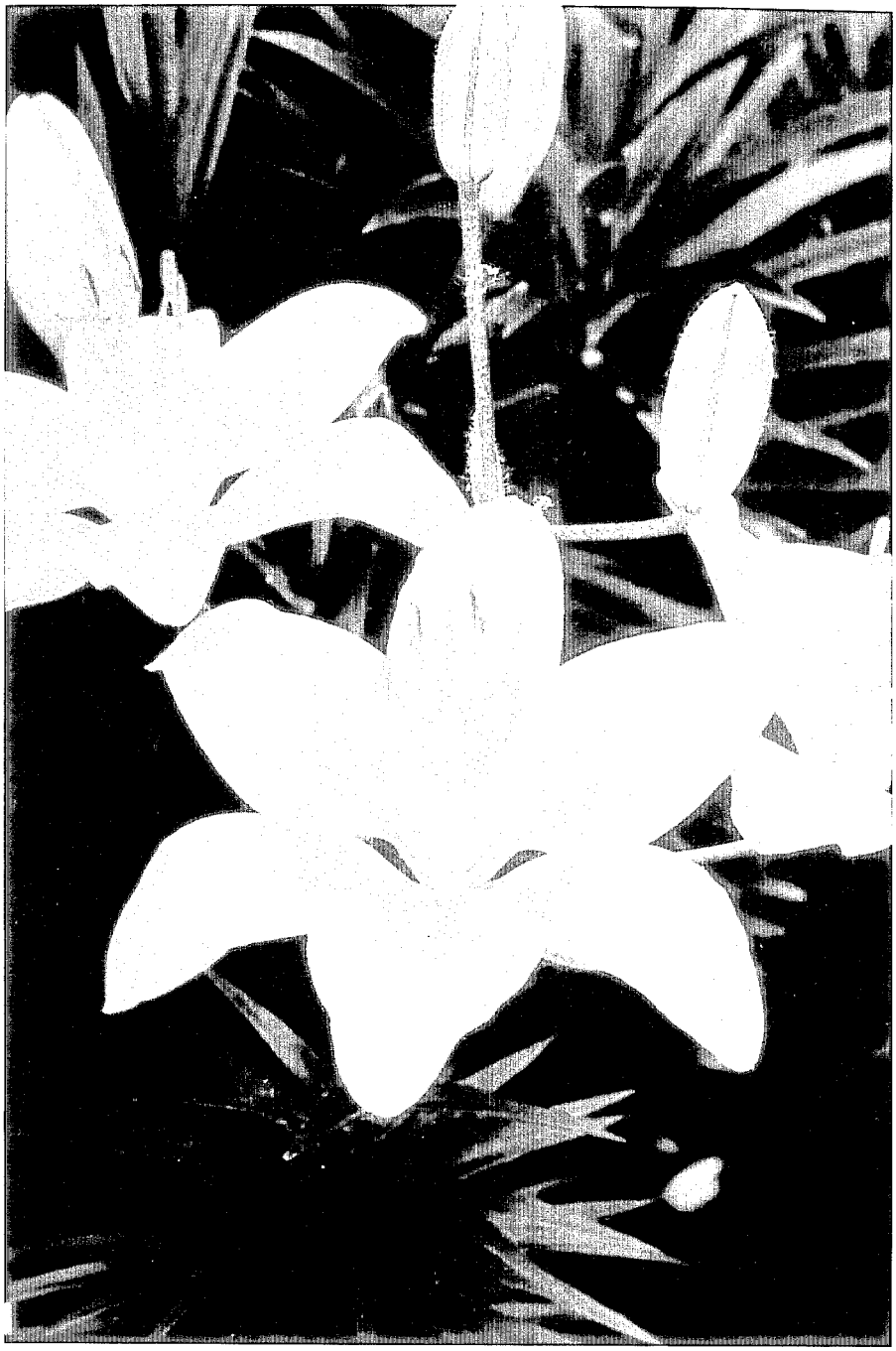

* * * * *